United States Patent [19]

Wu

[11] Patent Number: 4,889,862

[45] Date of Patent: Dec. 26, 1989

[54] FREEZE-DRIED PHARMACEUTICAL COMPOSITIONS OF PHENYLQUINOLINE CARBOXYLIC ACIDS

[75] Inventor: Chien-Chin Wu, Wilmington, Del.

[73] Assignee: E. I. Du Pont de Nemours and Company, Wilmington, Del.

[21] Appl. No.: 60,203

[22] Filed: Jun. 10, 1987

Related U.S. Application Data

[63] Continuation-in-part of Ser. No. 901,254, Aug. 28, 1986, abandoned.

[51] Int. Cl.$^4$ .................. A61K 31/47; A61K 47/00
[52] U.S. Cl. .................................. 514/311; 514/769; 514/784; 514/970
[58] Field of Search ............... 514/311, 182, 970, 769, 514/784

[56] References Cited

U.S. PATENT DOCUMENTS

| | | | |
|---|---|---|---|
| 4,036,954 | 7/1977 | Murakami et al. | 514/573 |
| 4,680,299 | 7/1987 | Hesson | 514/311 |

FOREIGN PATENT DOCUMENTS

| | | |
|---|---|---|
| 3329952 | 8/1983 | Fed. Rep. of Germany . |
| 59-076017 | 4/1984 | Japan . |

OTHER PUBLICATIONS

Remington's Pharmaceutical Sciences, 15th Ed. Maek Pub., pp. 1466 & 1483–1485.

"The Characterization of Sodium Cholate Solubilized Rhodopsin", R. A. Henselman & M. A. Cusanovich, Biochemistry, vol. 13, No. 25, 1974, pp. 5199–5203.

*Primary Examiner*—Douglas W. Robinson
*Assistant Examiner*—Raymond J. Henley, III

[57] ABSTRACT

Freeze-dried pharamceutical compositions of antitumor phenylquinoline carboxylic acids, such as 6-fluoro-2-(2'-fluoro-1'-biphenyl-4-yl)-3-methyl-4-quinolinecarboxylic acid, sodium salt, reconstitutable to stable, aqueous, injectable compositions are provided. These compositions use a stabilization system consisting essentially of bile salt, such as sodium cholate or sodium desoxycholate, and a base or buffer that will provide a pH of about 8.5–11 upon a aqueous reconstitution. Glycine is the preferred buffer.

10 Claims, No Drawings

FREEZE-DRIED PHARMACEUTICAL COMPOSITIONS OF PHENYLQUINOLINE CARBOXYLIC ACIDS

CROSS-REFERENCE TO RELATED APPLICATION

This application is a continuation-in-part of copending application Ser. No. 901,254, filed Aug. 28, 1986 now abandoned.

FIELD OF THE INVENTION

This invention relates to a freeze-dried pharmaceutical compositions and stable, aqueous, injectable compositions reconstitutable therefrom. More particularly this invention relates to such compositions which use bile salts in the stabilization system for antitumor phenylquinolinecarboxylic acids.

BACKGROUND OF THE INVENTION

Phenylquinolinecarboxylic acids are disclosed as antitumor agents in coassigned U.S. Application Ser. No. 727,808 filed Apr. 26, 1985, now U.S. Pat. No. 4,680,299 granted July 14, 1987. These agents are also described in EPO Published Application No. 0133,244, published Feb. 20, 1985. However, in order to avoid contamination or risk from spillage or aerosol inhalation during ampul opening, a freeze-dried powder is a preferred dosage form for these agents.

To prepare a freeze-dried product, it is required to make up a drug solution which can be filtered, filled into suitable containers, and lyophilized to form an elegant cake. Also, after being reconstituted, the drug solution should be free of particulates and be ready for intravenous administration.

The phenylquinolinecarboxylic acids, when in acid form, are insoluble in water. The solutions prepared with the salts of the acids are unstable and have a tendency to form precipitates after a short period of time. Precipitation occurs even at a concentration as low as 100 $\mu$g/ml while a solution up to 125 mg/ml is needed for product preparation. It is apparent that solubilizers which can enhance the solubility of these phenylquinolinecarboxylic acids are needed.

Solubilization techniques are known in the art, but such techniques depend on the drugs being formulated. For example, using a co-solvent or a complexation agent for drug solubility enhancement was found useful in some pharmaceutical applications. Such examples can be found in "Techniques of Solubilization of Drugs", edited by S. H. Yalkowsky, Chapter 3, page 91. However, these techniques are not practical for preparing freeze-dried compositions that are reconstituted to intravenous products. For example, co-solvents such as ethyl alcohol, benzyl alcohol and propylene glycol can solubilize a drug to a desirable concentration, but due to the liquid nature of these co-solvents, preparation of freeze-dried powders with these co-solvents is difficult. Attempts to use a complexation agent such as niacinamide up to a physiologically acceptable concentration with phenylquinonecarboxylic acids fails to prevent the acids from precipitation.

Another procedure which has been used to improve the solution stability with some drugs is to use micellar solubilization techniques with suitable solubilizers. However, to identify a useful solubilizer is a challenging task for parenteral formulators because the micelle from each solubilizer behaves differently. For example, the micelles formed from some commonly used solubilizers such as Tween®20, Tween®80, and Emulphor®719P and Pluronic®F-68 do not have enough solubilization capacity to prevent the quinolinecarboxylic acids from precipitating. Also, incorporating these solubilizers in the parenteral formulation can either result in a change in drug activity due to the inclusion of the drug into the hydrophobic micellar core or cause toxicity to increase due to the surface activity of these solubilizers.

U.S. Pat. No. 4,478,829, issued Oct. 23, 1984, describes the use of bile salts as surface active agents, in the same category as the Polysorbates, Triton®X100 and Pluronic®F-68 surfactants, in the preparation of lyophilized fibronectin which is readily reconstitutable with sterile water. Similarly, the bile salt sodium desoxycholate is described in published European Patent Application No. 141922-A1 in combination with freeze-drying to reduce turbidity in reconstituted clinical control sera.

U.S. Pat. No. 4,036,954, issued July 19, 1977, describes the use of a salt of desoxycholic acid as an addition in the lyophilization of a prostaglandin E group compound.

It is known that the freeze-drying technique can be used to convert a drug formulation from an aqueous mixture into a solid form. It is surprising to find that in this invention the antitumor phenylquinolinecarboxylic acid compounds can be successfully formulated into stable aqueous injectable compositions by employing a specially selected type of solubilizer in conjunction with the freeze-drying technique.

SUMMARY OF THE INVENTION

According to the present invention there is provided a powder pharmaceutical composition suitable for reconstitution into a parenteral solution consisting essentially of a freeze-dried mixture of (a) a salt of a drug which in free acid form has an aqueous solubility in the $\mu$g/ml range at room temperature, and (b) a stabilization system consisting essentially of (1) a bile salt and (2) a pharmaceutically acceptable base or buffer that will give a pH in the range of 8.5–11 upon aqueous reconstitution, the weight ratio of (a) to (b)(1) being at least about 1:0.1.

There is also provided a stable, injectable pharmaceutical composition comprising: an aqueous solution of 1 part by weight of a salt of a drug which in free acid form has an aqueous solubility in the $\mu$g/ml range at room temperature, at least about 0.1 part by weight of a bile salt per part of drug, and sufficient pharmaceutically acceptable base or buffer to provide a pH in the range of about 8.5–11.

DETAILED DESCRIPTION OF THE INVENTION

In this invention, it was discovered that bile salts, which are major breakdown products of cholesterol in humans, are useful solubilizers to prevent salts of phenylquinolinecarboxylic acids from precipitating during the preparation of bulk solution and upon reconstituting from the freeze-dried form. Drug solutions prepared with these solubilizers are stable and can be easily freeze-dried to form elegant cakes without change in potency. After being reconstituted with water for injection, the solution remained clear and suitable for intravenous administration. Further studies also indicated that there is little change in drug activity and toxicity when the drug and bile salt solubilizers were dissolved together in the solution.

The freeze-dried powder formulation described in this invention consist essentially of an active antitumor ingredient, a salt of a phenylquinolinecarboxylic acid, preferably 6-fluoro-2-(2'-fluoro-1'-biphenyl-4-yl)-3-methyl-4-quinolinecarboxylic acid, sodium salt, or 2-(1,1'-biphenyl-4-yl)-5-chloro-3-methyl-4-quinolinecarboxylic acid, sodium salt, and a stabilization system. The stabilization system consists essentially of a bile salt solubilizer and a pharmaceutically acceptable buffer or base that will adjust pH to 8.5–11 in aqueous solution.

While any salt of the phenylquinolinecarboxylic acids described in EP-133,244-A1 can be used, the preferred acid salts are those described above. The description of such acids in EP-133,244-A1 is hereby incorporated by reference.

The bile salts useful in the stabilization system are preferably sodium cholate or sodium desoxycholate. Other alkali metal salts (lithium, potassium) or organic salts can also be used. Salts of other bile acids are also useful. These include dehydrocholic acid, lithocholic acid, hydrodeoxycholic acid, chenodeoxycholic acid, glycodeoxycholic acid, taurodeoxychloric acid, glycocholic acid, and taurocholic acid.

Any pharmaceutically acceptable base or buffer can be used in the compositions that will give an initial aqueous pH or a pH upon aqueous reconstitution in the range of about 8.5–11, preferably a pH of about 9. Useful buffers and bases include sodium glutamate, sodium phosphate, glycine, sodium hydroxide, triethanolamine, and sodium carbonate. Preferred materials are glycine or sodium hydroxide. Glycine is particularly preferred.

The amounts of materials in the compositions are based on the drug, e.g., the salt of a phenylquinolinecarboxylic acid. For every 1 part by weight of the drug, at least about 0.1 part by weight of bile salt is required. Typically, the preferred weight ratio of drug to bile salt is in the range of about 1:0.1 to 1:0.8.

The invention can be further understood by the following examples.

EXAMPLE 1

Freeze-dried Formulation Containing 6-Fluoro-2-(2'-fluoro-1'-biphenyl-4-yl)-3-methyl-4-quinolinecarboxylic Acid, Sodium Salt Each 10 ml vial contained the title compound (100 mg), sodium cholate (40 mg), and glycine (40 mg).

For Manufacture of 250 Vials:

The title compound (25 g) was suspended in a solution of sodium cholate (10 g) and glycine (10 g) in water for injection (950 ml). The pH of the resulting suspension was adjusted to 9.0–9.5 with 1N NaOH and the mixture was stirred until it was clear. The solution was then adjusted to 1000 ml by adding water for injection with stirring and then filtered through a 0.22 μm filter. Each 10 ml vial was aseptically filled with 4 ml of the filtered solution.

The vials were placed in a lyophilizer and frozen to −40° to −45° C. for two hours. The condenser was turned on and the temperature allowed to reach −60° C. The vials were then vacuumed at 50–100 milliTorr at 20° C. for 24 hours. Finally, the vials were dried at 45° C. for two or more hours to give an elegant white cake which was reconstituted with water (4 ml) for injection to a stable solution for intravenous use.

The 24-hour stability data for the reconstituted solution of the title compound is shown in Table I.

TABLE I

| Time (hours) | % of Drug Remaining | Physical Appearance |
| --- | --- | --- |
| 0 | Mean 99.4<br>S.D. ± 0.1 | Clear solution |
| 6 | Mean 100.0<br>S.D. ± 0.2 | Clear solution |
| 24 | Mean 99.2<br>S.D. ± 0.2 | Clear solution |

Drug concentrations were determined by high pressure liquid chromatography (HPLC). The mean value is based on four separate aliquots taken from a composite sample.

EXAMPLE 2

Freeze-dried Formulation Containing 2-(1,1'-Biphenyl-4-yl)-5-chloro-3-methyl-4-quinolinecarboxylic Acid, Sodium Salt Each 10 ml vial contained the title compound (100 mg), sodium desoxycholate (50 mg), and glycine (50 mg).

This formulation was prepared in a manner similar to that described in Example 1. A powder of similar properties was obtained.

EXAMPLE 3

Freeze-dried Formulation Containing 6-Fluoro-2-(2'-fluoro-1,1'-biphenyl-4-yl)-3-methyl-4-quinolinecarboxylic Acid, Sodium Salt Each 10 ml vial contained the title compound (100 mg), sodium cholate (80 mg), and sodium hydroxide (enough to make pH 9.0).

This formulation was prepared in a manner similar to that described in Example 1. A powder of similar properties was obtained.

EXAMPLE 4

Freezed-dried Formulation Containing 6-Fluoro-2-(2'-fluoro-1'-biphenyl-4-yl)-3-methyl-4-quinolinecarboxylic Acid, Sodium Salt Each 20 ml vial contained the title compound (500 mg), sodium cholate (80 mg), and glycine (80 mg).

For manufacture of 250 vials:

The title compound (125 g) was suspended in a solution of sodium cholate (20 g), and glycine (20 g) in water for injection (1950 ml). The pH of the resulting suspension was adjusted to 9.0–9.5 with 1N NaOH and the mixture was stirred until it was clear. The solution was then adjusted to 2000 ml by adding water for injection with stirring and then filtered through a 0.22 μm filter. Each 20 ml vial was aseptically filled with 8 ml of the filtered solution.

The vials were placed in a lyophilizer and frozen to −40° to −45° C. for six hours. The condenser was turned on and the temperature allowed to reach −60° C. The vials were then vacuumed at 50–100 milliTorr at 20° C. for 24 hours. Finally, the vials were dried at 45° C. for four more hours to give an elegant white cake which was reconstituted with water (8 ml) for injection to a stable solution for intravenous use.

EXAMPLE 5

Stability Studies on Freeze-dried
6-Fluoro-2-(2'-fluoro-1'-biphenyl-4-yl)-3-methyl-4-quinolinecarboxylic Acid, Sodium Salt The title compound was formulated as described in Example 1. The freeze-dried powder was sealed in 10 ml vials and stored at various conditions for stability observation. As shown in Table II, the formulated samples are chemically stable. However, by visual inspection, a light brown color developed upon exposure to excessive light.

TABLE II

Initial Assay: 100.4 mg of the title compound in 10 ml clear glass vial with rubber stopper
Figures listed as a percentage of initial assay

| STORAGE TIME | STORAGE CONDITIONS | | | | | |
|---|---|---|---|---|---|---|
| | 25° C. | 40° C. | 50° C. | 60° C. | 90% Relative Humidy (RH) | 600 Footcandle (FC) |
| 4 weeks | — | — | — | 100.2 | — | 100.2 |
| 8 weeks | — | 100.3 | 99.7 | 99.8 | — | 99.2 |
| 12 weeks | 100.1 | 99.5 | 100.5 | 100.0 | 100.2 | 99.3 |
| 6 months | 99.6 | 99.4 | — | — | — | — |

EXAMPLE 6

In Vivo Antitumor Activity of Formulated
6-Fluoro-2-(2'-fluoro-1,1'biphenyl-4-yl)-3-methyl-4 quinolinecarboxylic Acid, Sodium Salt A solution (1 ml) containing the title compound (25 mg), sodium cholate (10 mg), and glycine (10 mg) was prepared with the same composition as that of the reconstituted solution described in Example 1. Then distilled water (4 ml) was added to the above to make 50 mg/kg solution. Serial two-fold dilutions were made in distilled water from the 50 mg/kg solution for the remaining three concentrations. An unformulated control solution was prepared by dissolving the title compound in distilled water and was used while it remained clear.

The antitumor activity of the formulated and unformulated material against L1210 leukemia in mice is shown in Table III. The test was carried out as follows. On day 0, CDF1 mice were injected with $1 \times 10^5$ L1210 murine leukemia cells intraperitoneally. On day 1 formulated and unformulated title compound were injected intraperitoneally and the injections continued, once daily through day 9. Mice were observed until death.

TABLE III

Survival Time: % T/C (mean day of death for treated animals/mean day of death for control animals × 100)

| Title Compound | 50 | 25 | 12.5 | 6.25 |
|---|---|---|---|---|
| | mg/kg/day × 9 days | | | |
| formulated* | 114 | 180 | 175 | 171 |
| unformulated** | 89 | 169 | 167 | 156 |

*vehicle control animals survived 8.5 days (0.2% sodium cholate, 0.2% glycine in distilled H₂O)
**vehicle control animals survived 9.0 days (distilled H₂O)

These testing results show that sodium cholate and glycine have no effect on the antitumor activity of the title compound.

EXAMPLE 7

Safety Comparison of Formulated
6-Fluoro-2-(2'-fluoro-1'-biphenyl-4-yl)-3-methyl-4-quinolinecarboxylic Acid, Sodium Salt in Distilled Water and in 1% Sodium Cholate/1% Glycine A comparative test was performed on the title compound to evaluate possible lethality differences between compositions described herein and compositions prepared by dissolving in water. The title compound was formulated into a freeze-dried composition as in Example 1 and reconstituted with water prior to injection.

The two solutions of the title compound were parenterally administered to female $B_6C_3F_1$ mice weighing between 17–22 grams at single dosages of 0, 120, 144, 173, and 200 mg/kg. Following compound administration, mortality was evaluated twice daily for 14 days.

$LD_{50}$ values, their corresponding 95% Confidence Intervals and the slope of the response curves are as follows:

| Vehicle containing Title Compound | $LD_{50}$ | 95% C.I. | Slope |
|---|---|---|---|
| D.I. H₂O, pH = 8.5 | 156 | 141–173 | 1.18 |
| 1% Na Cholate/Gly, pH = 9.0 | 141 | 124–159 | 1.27 |

Additionally, ten female $B_6C_3F_1$ mice were administered a single dose of the 1% sodium cholate/glycine (pH=9.0) vehicle intravenously at 10 mL/kg. No mortalities were observed as a result of this control vehicle administration.

What is claimed is:

1. A powder pharmaceutical composition suitable for reconstitution into an injectable solution for intravenous or intraperitoneal use, consisting essentially of a freeze-dried mixture of (a) a sodium or potassium salt of a phenylquinoliine carboxylic acid useful as an anti-tumor agent, and (b) a stabilization system consisting essentially of (1) a bile salt and (2) a pharmaceutically acceptable base or buffer that will give a pH in the range of 8.5–11 upon aqueous reconstitution, the weight ratio of (a) to (b)(1) being at least about 1:0.1.

2. The powder composition of claim 1 wherein the weight ratio of (a) to (b)(1) is in the range of about 1:0.1 to 1:0.8.

3. The powder composition of claim 2 wherein the bile salt (b)(1) is cholic acid or desoxycholic acid.

4. The powder composition of claim 3 wherein the base or buffer (b)(2) is glycine or sodium hydroxide sufficient to give a pH upon aqueous reconstitution of about 9.

5. The powder composition of claim 1 wherein the phenylquinolinecarboxylic acid salt is 6-fluoro-2-(2'-fluoro-1'-biphenyl-4-yl)-3-methyl-4-quinolinecarboxylic acid, sodium salt or 2-(1,1'-biphenyl-4-yl)-5-chloro-3-methyl-4-quinolinecarboxylic acid, sodium salt.

6. A powder pharmaceutical composition suitable for reconstitution into an injectable solution for intravenous or intraperitoneal use, consisting essentially of a freeze-dried mixture of (a) 1 part by weight of 6-fluoro-2-(2'-fluoro-1'-biphenyl-4-yl)-3-methyl-4-quinolinecarboxylic acid, sodium salt, and (b) a stabilization system consisting essentially of (1) about 0.1–0.8 parts by weight of sodium cholate, and (2) sufficient glycine to give a pH of about 9 upon aqueous reconstitution.

7. A stable, injectable pharmaceutical composition for intravenous or intraperitoneal use, comprising: an aqueous solution of 1 part by weight of a sodium or potassium salt of phenylquinoline carboxylic acid useful as an anti-tumor agent, at least about 0.1 part by weight of a bile salt per part of drug, and sufficient pharmaceutically acceptable base or buffer to provide a pH in the range of about 8.5–11.

8. The injectable composition of claim 7 wherein the bile salt is sodium cholate or sodium desoxycholate at a weight concentration in the range of about 0.1 to 0.8 parts per part of drug.

9. The injectable composition of claim 8 wherein the base or buffer is glycine or sodium hydroxide sufficient to give a pH of about 9.

10. The injectable composition of claim 7 wherein the phenylquinolinecarboxylic acid salt is 6-fluoro-2-(2'-fluoro-1'-biphenyl-4-yl)-3-methyl-4-quinolinecarboxylic acid, sodium salt or 2-(1,1'-biphenyl-4-yl)-5-chloro-3-methyl-4-quinolinecarboxylic acid, sodium salt.

* * * * *